(12) United States Patent
Kobayashi et al.

(10) Patent No.: US 7,749,750 B2
(45) Date of Patent: Jul. 6, 2010

(54) CULTURING APPARATUS

(75) Inventors: Toyoshige Kobayashi, Hatoyama (JP); Kazutoshi Kan, Kaiwagoe (JP); Akira Koide, Inashiki (JP); Hideaki Sakai, Kawasaki (JP)

(73) Assignee: Hitachi, Ltd., Tokyo (JP)

( * ) Notice: Subject to any disclaimer, the term of this patent is extended or adjusted under 35 U.S.C. 154(b) by 974 days.

(21) Appl. No.: 11/192,023

(22) Filed: Jul. 29, 2005

(65) Prior Publication Data

US 2006/0115893 A1 Jun. 1, 2006

(30) Foreign Application Priority Data

Nov. 26, 2004 (JP) .............................. 2004-341399

(51) Int. Cl.
*C12M 1/22* (2006.01)
*C12M 3/00* (2006.01)

(52) U.S. Cl. .............. 435/305.2; 435/289.1; 435/305.3; 422/100; 422/103; 422/104

(58) Field of Classification Search .............. 435/305.2, 435/305.3, 307.1; 141/16, 22, 28, 44, 236, 141/244, 246, 287, 293; 222/40, 153.05, 222/472, 609, 555; 347/214, 216
See application file for complete search history.

(56) References Cited

U.S. PATENT DOCUMENTS

| 4,228,243 | A | * | 10/1980 | Iizuka ..................... 435/294.1 |
| 4,661,455 | A | * | 4/1987 | Hubbard ..................... 435/401 |
| 4,839,292 | A | * | 6/1989 | Cremonese .............. 435/297.2 |
| 5,153,131 | A | * | 10/1992 | Wolf et al. .................. 435/401 |
| 6,455,310 | B1 | * | 9/2002 | Barbera-Guillem ......... 435/383 |
| 2003/0040104 | A1 | * | 2/2003 | Barbera-Guillem ...... 435/286.2 |
| 2004/0152186 | A1 | | 8/2004 | Kan et al. |

FOREIGN PATENT DOCUMENTS

| JP | 2002-262856 | 9/2002 |
| JP | 2004-129568 | 4/2004 |

* cited by examiner

*Primary Examiner*—William H Beisner
*Assistant Examiner*—Michael Hobbs
(74) *Attorney, Agent, or Firm*—Antonelli, Terry, Stout & Kraus, LLP.

(57) ABSTRACT

A culturing apparatus has a culture vessel having a first elastic seal bonded on its upper surface and a culture space formed thereon, and a joint for supplying solution such as a medium to the culture vessel and a second elastic seal having microprojection formed at the lower face. The first elastic seal has a valve for supplying or discharging solution. The second elastic seal is formed with microprojection at the position corresponding to a valve for preventing a spill. The culture vessel and the joint are sucked between the first elastic seal and the second elastic seal, thereby forming an integral seeding device.

12 Claims, 5 Drawing Sheets

CULTURING APPARATUS

CLAIM OF PRIORITY

The present application claims priority from Japanese application serial JP2004-341399 filed on Nov. 26, 2004, the content of which is hereby incorporated by reference into this application.

BACKGROUND OF THE INVENTION

The present invention relates to a culturing apparatus that cultures cells.

Japanese Patent Laid-Open No. 2002-262856 discloses an example of a conventional automated cell culture. In a cell culturing apparatus disclosed in this application, an automatic medium exchanging device is provided with an incubator, a medium exchanging robot and a management computer, in order to automatically exchange a medium. The management computer takes out a culture tray, on which cells are cultured, from the incubator to the outside by a carrier robot or the like, discharges a liquid medium in the culture tray with a needle, injects new liquid medium by the needle, and puts the culture tray into the incubator.

Japanese Patent Laid-Open No. 2004-129568 discloses an example of a culture vessel, in a cell culture, that reduces the infection and achieves the effective cell culture with a simple configuration. The culture vessel disclosed in this application has a vessel body whose inside is sterilized and that has a film disposed at its portion and at least one tube that communicates with the inside of this vessel body and is made of a thermally depositable material whose leading end is closed.

The most important subject upon culturing cells are to prevent the cultured cell from being infected by dust, bacteria, virus, or the like. In order to prevent the infection, it is required that a series of processes in the cell culture such as cell seeding or exchange of a medium is performed in a sterilized state so as to prevent contaminants from being entered. A cell culture or processing is currently made by skilled technicians in a cell processing center at a large-scale culture facility composed of sterilized each facility by using a technique provided by GMP (GOOD MANUFACTURING PRACTICE). In this infection management, it is difficult to enhance productivity and reduce cost for industrialization.

In order to eliminate this inconvenience, an automated culturing apparatus disclosed in Japanese Patent Laid-Open No. 2002-262856 has been proposed wherein an operation same in level as that carried out by a skilled technician with a quality retained is possible by using an automated technique. The device disclosed in this application performs cells seeding or exchange of a medium by using a driving device such as a robot arm, so that it requires a clean space or control system considering an operating range of the arm, thereby making the whole device extremely large-scale.

Since a current culture tool such as a culture dish or the like is open to the outer space, safety cannot be assured so long as germs of various sorts in the space around a seeding device are reduced. Therefore, the automated culturing apparatus can only be installed in a facility, the whole of which is sterilized, such as a processing center, so that a large sterilizing system is required to produce a small tissue from cultured cells.

The infection can be prevented by closing the culture space to remove the connection with the outside in order to eliminate such inconvenience, as disclosed in JP2004-129568. A device can be miniaturized by using the culture vessel disclosed in this application, but a perfect closed system makes it difficult to move substances into or from an outer space.

BRIEF SUMMARY OF THE INVENTION

The present invention is accomplished in view of the aforesaid inconvenience of the conventional technique, and its object is to simply perform the cell seeding and exchange of medium, while preventing the infection from the outside in the cell culture.

The feature of the invention for accomplishing the aforesaid object is to comprise a culture vessel having a culture vessel member to which a culture space for culturing cells are formed and a first elastic seal arranged above the culture space of the culture vessel member, and a joint having a joint member provided with supplying means for supplying solution such as a medium to this culture vessel and a second elastic seal bonded to the joint member, wherein the culture vessel is detachably mounted to the joint by using suction means formed on the joint.

In this feature, the suction means has a suction pad attached to the second elastic seal and a pump that communicates with this suction pad to exert suction force, and the first elastic seal has cutout at plural sections, this cutout being used as a valve. Further, holes are formed on the second elastic seal at the positions corresponding to cutouts, wherein a ring-like step portion having a predetermined thickness is formed around each hole, whereby the first elastic seal is pushed to penetrate through the second elastic seal, to attach a tube, which can supply the solution into the culture space, to the joint member.

Another feature of the invention for accomplishing the aforesaid object is a culturing apparatus comprising a culture vessel having a first elastic seal bonded to its upper face and having the culture space formed therein; and a joint provided with supplying section for supplying solution such as a medium to the culture vessel and having bonded to its lower face a second elastic seal having a microprojection; wherein the first elastic seal has a valve for supplying or discharging the solution, and second elastic seal has a microprojection formed at the position corresponding to the valve for preventing a spill, wherein the culture vessel and the joint are sucked between the first elastic seal and the second elastic seal to compose an integrally formed seeding device.

In this feature, adsorbing means is provided at the second elastic seal and a suction pump is connected to this adsorbing means via a tube, wherein the culture vessel and the joint are attached to and detached from each other between the first elastic seal and the second elastic seal by the operation of the suction pump. It is preferable that a water-repellant process is provided on the surface of the valve and the surface of the microprojection. Further, it is desirable that a base on which the seeding device is placed is provided, wherein a projection is formed on the base at the position corresponding to the width of the culture vessel, a groove is provided at the side section of the culture vessel into which the projection is engaged, and the seeding device can be held by engaging the projection into the groove upon the culture.

In the aforesaid feature, an arm may be provided and a rotation axis is connected to the leading end of this arm, wherein, when solution such as a medium is injected into or discharged from the culture space, the rotation axis may be operated such that the seeding device integrally formed by the adsorbing means is inclined from its horizontal direction. It is preferable that plural valves are formed at the position corresponding to the outside of the culture space, wherein the solution is supplied from the valve section positioned downward and the solution is discharged from the valve section positioned upward, when the solution is exchanged.

According to the present invention, a detachable joint is provided at a seeding device, and this joint is sealed by a resin, whereby an exchange of a medium or cell seeding can be easily performed while preventing the infection from the outside. Further, liquid is injected from below with the attached joint and seeding device inclined in the vertical direction, whereby the liquid is assuredly injected into the culture space. The present invention also provides an effect that bubbles included in the culture space are vented at this time.

BRIEF DESCRIPTION OF THE SEVERAL VIEW OF THE DRAWING

FIGS. 1 to 5 are views showing one embodiment of a seeding device according to the present invention, wherein FIG. 1 is its perspective view:;

FIG. 2 is its exploded perspective view;

FIG. 3 is a partial detailed sectional view;

FIG. 4 is its front view showing a state of removing a culture vessel;

FIG. 5 is a front view when the seeding device is inclined; and

DETAILED DESCRIPTION OF THE INVENTION

Figure 6:
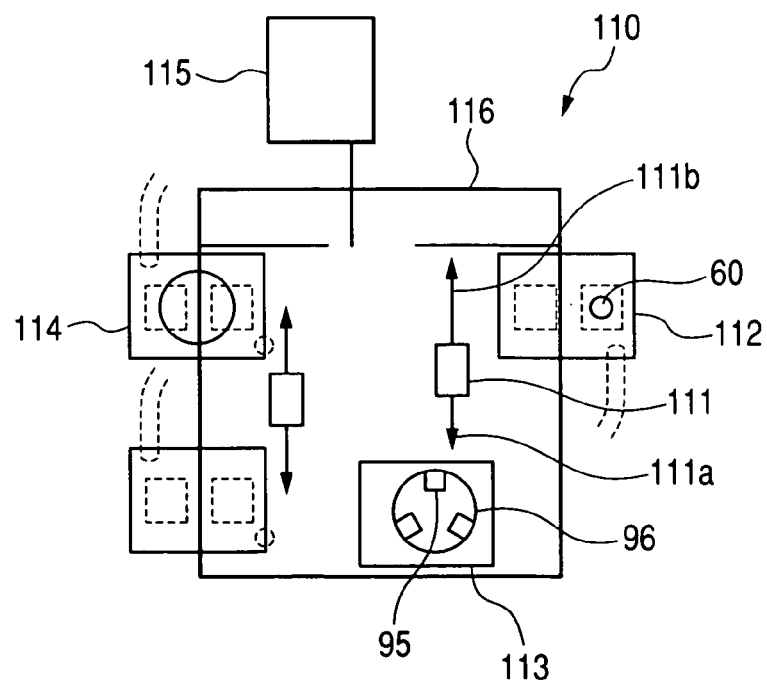
FIG. 6 is a top plan view of a culturing apparatus according to one embodiment of the present invention.

One embodiment of a culturing apparatus according to the invention will be explained hereinafter with reference to drawings. FIG. 6 is a top plan view of a culturing apparatus 110. The culturing apparatus 110 has a culture vessel inserting portion 112 for inserting a culture vessel 60 into the sterilized culturing apparatus 110 and a culture chamber 113 for culturing cells in the culturing vessel 60. The culture vessel 60 inserted from the culture vessel inserting portion 112 into the culturing apparatus 110 is transported to the culture chamber 113 by moving one of a pair of joint holder positioning sections 111, that are arranged in the culturing apparatus 110 so as to be substantially parallel to each other, in the forward and rearward directions 111a and 111b.

A turntable 96 having a driving system provided at its back face is arranged in the culture chamber 113. Plural bases 95 are spaced in the circumferential direction on the turntable 96. When cells are put into the culture vessel 60 at the beginning of the culture, the other one of the joint holder positioning sections 111 moves in the forward and rearward directions 111a and 111b, so that cell suspension put from a cell inserting section 114 provided at the culturing apparatus 110 is injected into the culture vessel 60. The culture vessel 60 to which the cell suspension is injected is returned to the culture chamber 113, whereby the culture is progressing. When a medium is exchanged, a medium supplied from a medium supplying section 115 is injected into the culture vessel 60 held by the joint holder positioning sections 111. The medium supplying section 115 is placed at the outside of a sterilized draft 116. When the culture is completed, the joint holder positioning sections 111 returns the culture vessel to the culture vessel inserting section 112 or a culture vessel removing section separately provided.

Figure 1:
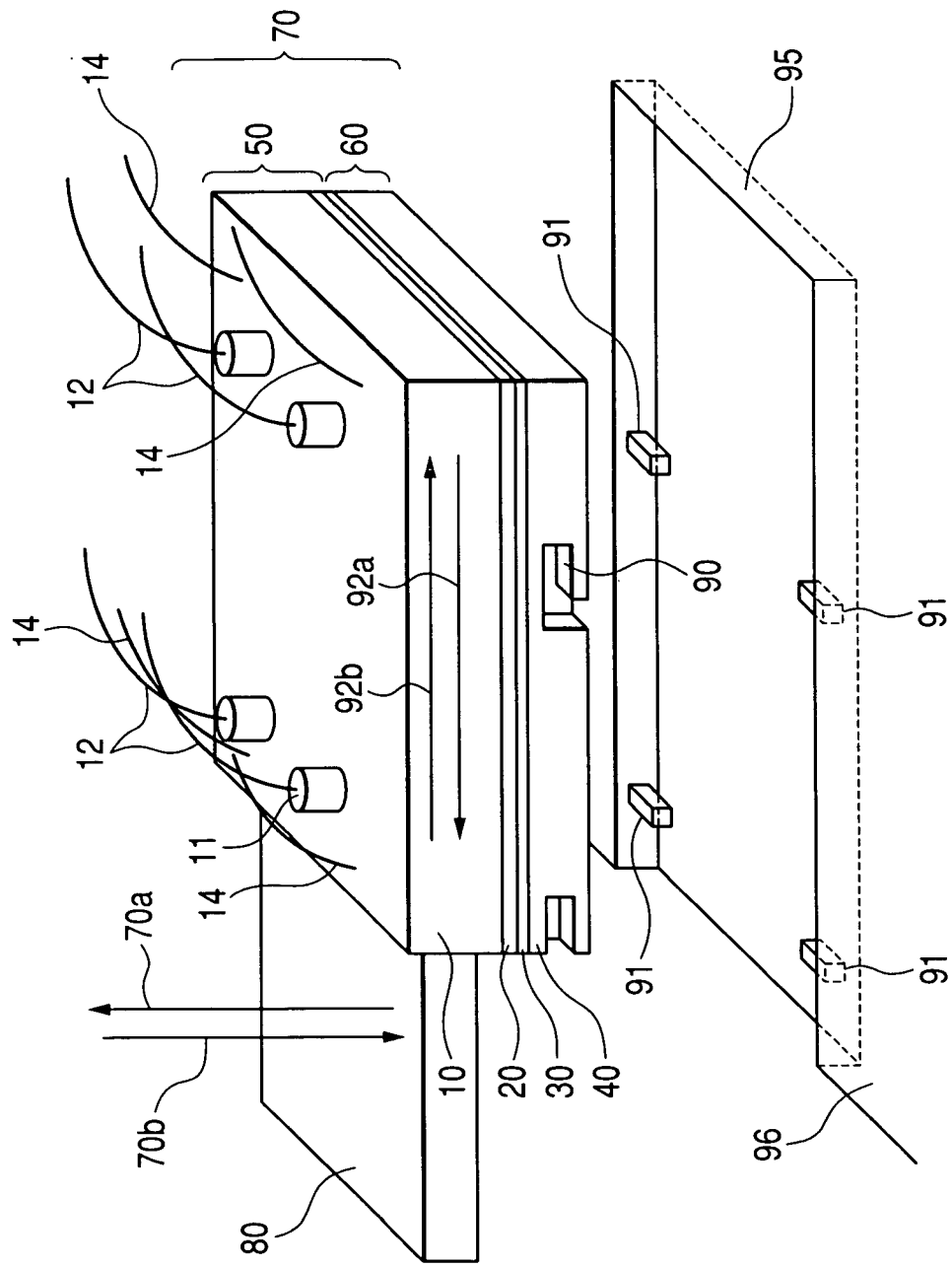
Figure 2:
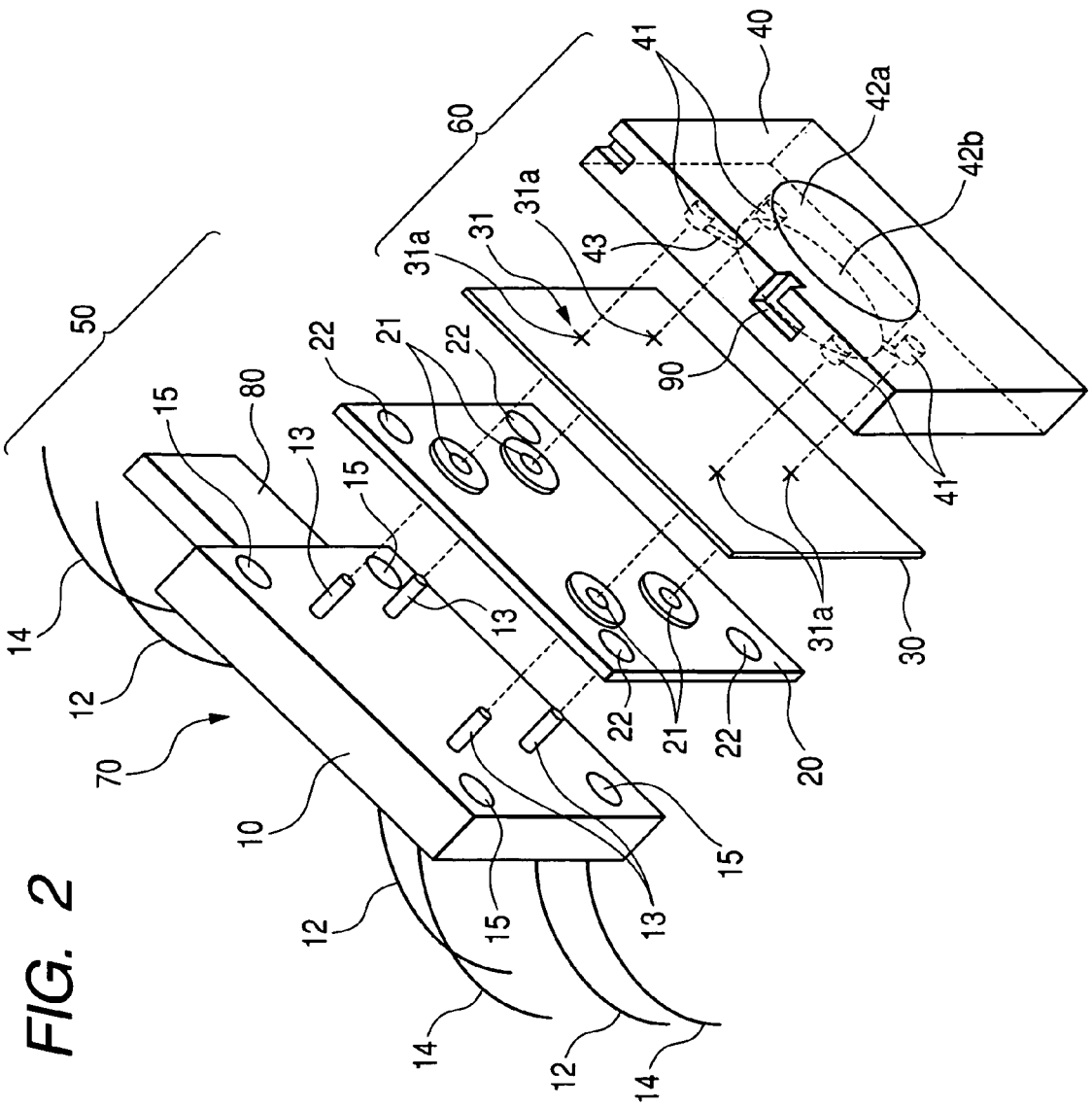
Figure 3:
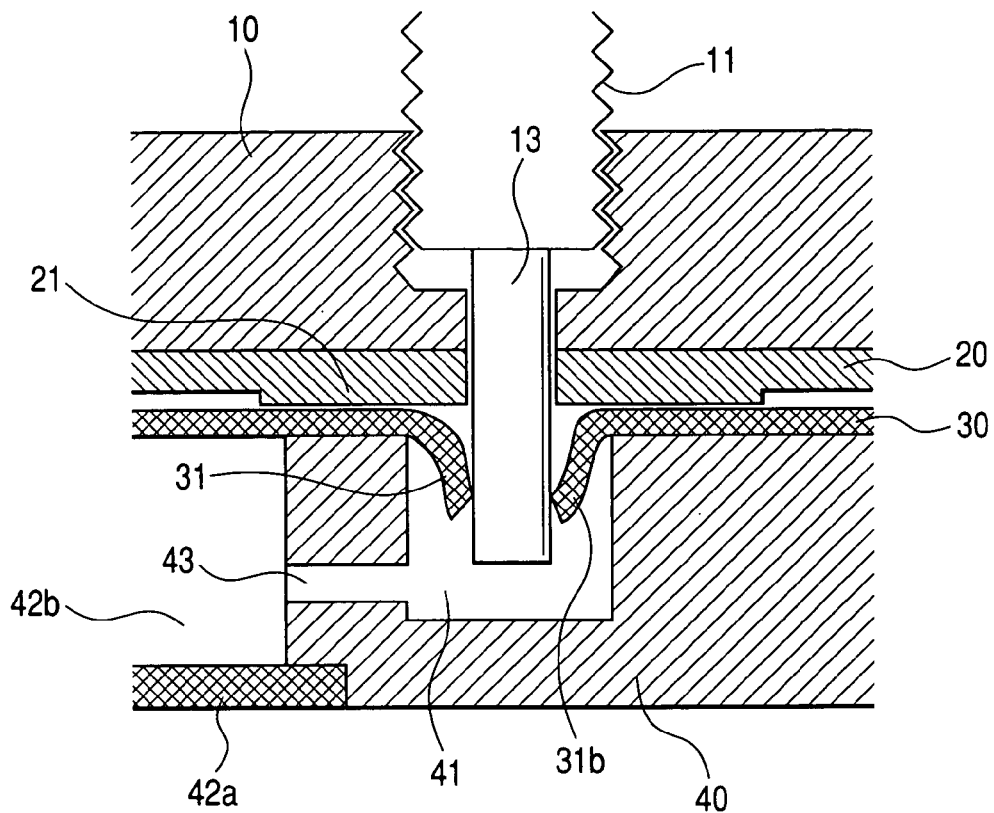

The state of a cell seeding or exchange of a medium will be explained with reference to FIGS. 1 to 5. FIG. 1 is a perspective view showing a state in which a seeding device 70 having the culture vessel 60 and a joint 50 integrally formed is attached on the turntable 96. FIG. 2 is an exploded perspective view of the seeding device 70 shown in FIG. 1. FIG. 3 is a partial detailed sectional view of the seeding device 70. The seeding device 70 has the culture vessel 60 having a vessel member 40 to which a culture space 42b is formed at its center, and the joint 50 that is arranged on the culture vessel 60 for introducing or discharging the culture liquid into or from the culture space 42b.

The vessel member 40 has a shape of thin rectangular parallel-epiped, and has the circular hollow culture space 42b formed at its center. A film 42a is attached to the bottom face of the vessel member 40 with an adhesion. Four locking holes 41 are formed around the circular space of the vessel member 40. Formed in the vicinity of the bottom face of the locking holes 41 is a flow channel 43 for communicating the culture space 42b with the locking holes 41.

A rectangular first elastic seal 30 having valves 31 formed at the position corresponding to each locking hole 41 is held at the upper face of the vessel member 40 with an adhesion. The first elastic seal is made of a viscoelastic material such as a silicon resin, wherein each of the valves 31 is a cross cutout formed at this viscoelastic material. The vessel member 40 and the first elastic seal 30 compose the culture vessel 60.

The joint 50 has a rectangular second elastic seal 20 arranged at the upper face of the culture vessel 60 and a joint member 10 that is made by fixing the second elastic seal 20 with an adhesion to be formed into a thin rectangular parallel-epiped. The second elastic seal 20 is made of a viscoelastic material such as a silicon resin. The second elastic seal 20 has annular microprojections 21, each being formed at the position opposite to the first elastic seal 30 and corresponding to each of the locking holes 41 formed at the vessel member 40. Holes 22 for a suction pad whose detail will be explained later are formed at the corner sections of the second elastic seal 20.

The joint member 10 is formed into a thin rectangular parallel-epiped and has four corner sections. Attached to the bottom face thereof are horn-like adsorbing pads 15 at the position corresponding to each of the holes 22 for a suction pad formed on the second elastic seal 20. Through-holes to which tubes 13 fitted to the locking holes 41 on the vessel member 40 are attached are formed on the bottom face of the joint member 10. As shown in FIG. 3, each through-hole is a stepped through-hole, wherein the upper hole is a threaded hole to which a fitted connector 11 is attached.

A tube 12 that can supply cell suspension, medium or chemical is detachably connected to the connector 11. Holes that communicate with the back face of the adsorbing pads 15 are also formed on the joint member 10. A suction tube 14 is fitted to each hole. Further, an arm 80 is attached to one side face of the joint member 10.

The joint 50 and the culture vessel 60 are made integral by a suction from the suction tubes 14, thereby composing the seeding device 70. The integrated seeding device 70 is fixed on the base 95 by an engagement between projections 91 formed on the base 95 and grooves 90 formed at the periphery section at the bottom section of the culture vessel 60.

A culture method by using the seeding device 70 having the aforesaid configuration will be explained hereinafter. Firstly, the state of adsorbing the culture vessel 60 to the joint 50 will be explained by using FIG. 3. Holes 41 for tubes 13 are formed on the culture vessel member 40, so that, if the culture vessel member 40 is handled as it is opened, it may be infected by germs or the like from the outside. Further, there is a fear that the environment may be polluted by a liquid spill from the holes 41. New tubes 13 are inserted into the holes 41 formed on the vessel member 40, every time a medium is exchanged, in order to prevent the infection. However, this increases the exchange frequency of tubes 13. Accordingly, it is necessary that the tubes 13 and holes 41 are assuredly sealed, even if the exchange frequency is increased, and that the holes 41 are automatically closed so as not to cause a liquid spill from the holes 41 even if the tubes 13 are removed. In view of this, the following seal is used in order to prevent that the inside of the culture vessel 60 is infected.

Specifically, in order to enhance adhesiveness and liquid spill prevention performance upon attaching or detaching the culture vessel 60 and the joint 50, the second elastic seal 20 is adhered onto the bottom face of the joint member 10 and the first elastic seal 30 is adhered onto the upper face of the culture vessel member 40. Then, the first elastic seal 30 is brought into intimate contact with the second elastic seal 20 by using a suction pump. A viscoelastic material is used for these seals 20 and 30 for enhancing adhesiveness between the second elastic seal 20 and the first elastic seal 30.

A valve 31 composed of a slit 31a is formed on the first elastic seal 30 for preventing the inclusion of germs or liquid spill from the holes 41, and for serving as a cover that automatically closes the hole 41 when the tube 13 is not inserted into the hole 41. A seal member 31b that is pushed downward from the slit 31a upon the insertion of the tube 13 is recovered by elastic force when the tube 13 is not inserted into the hole 41, whereby the valve 31 keeps its closed state. As a result, a liquid spill can be prevented.

When the tube 13 is inserted into the slit for the culture, the seal member 31b is downwardly spread out, so that the valve 31 is opened. The seal member 31b composing the valve 31 is brought into intimate contact with the tube 13 with elastic force, so that the liquid spill and reversed flow are prevented. It should be noted that water-repellant process is provided for the valve 31 for preventing the liquid spill and infection.

On the other hand, annular microprojections 21 are formed around the holes for the tubes 13 of the second elastic seal 20. They are used for adsorption between the first elastic seal 30 and the second elastic seal 20. When the joint 50 and the culture vessel 60 are adsorbed to each other, vacuum adsorption is performed by using the adsorbing pad 15 shown in detail in FIG. 4. The adsorbing pad 15 is connected to a suction pump not shown via the suction tube 14. Upon the suction, the microprojection 21 is pushed toward the culture vessel 60 to enhance the adhesiveness at the seal section formed around the hole 41.

Since the microprojections 21 are formed on the second elastic seal 20, the contact area between the first elastic seal 30 and the second elastic seal 20 is reduced, thereby increasing the contact pressure at the contact section. On the other hand, if the microprojections 21 are not formed, the contact pressure between the first elastic seal 30 and the second elastic seal 20 is reduced, thereby deteriorating the sealing performance around the tube 13.

Further, providing the microprojections 21 facilitates the removal of the culture vessel 60 from the joint 50. The first and second elastic seal members 30 and 20 have excellent adhesiveness since they are made of viscoelastic material. The step of each of the microprojection 21 prevents that the sections other than the seal section, i.e., the annular microprojections 21, are unnecessarily brought into intimate contact with the culture vessel 60. The formation of the microprojections 21 prevents the liquid spill between the joint 50 and the culture vessel 60, and further prevents that the liquid remains in the vicinity of the tube 13 to pollute the surroundings when the joint 50 is removed. Moreover, the water-repellant process is provided on the microprojections 21, so that there is no chance that the medium adheres to the microprojections 21.

Figure 4:
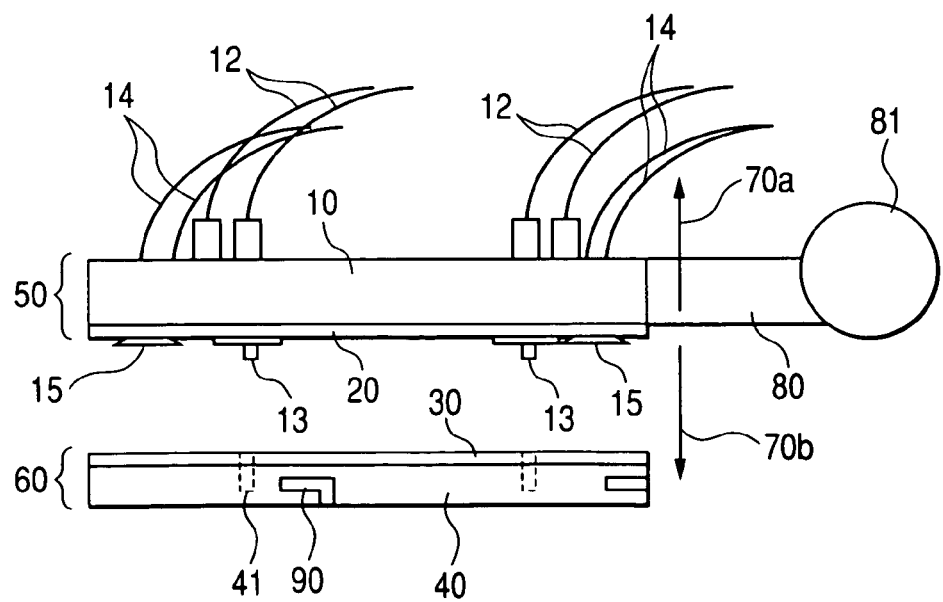
Figure 5:
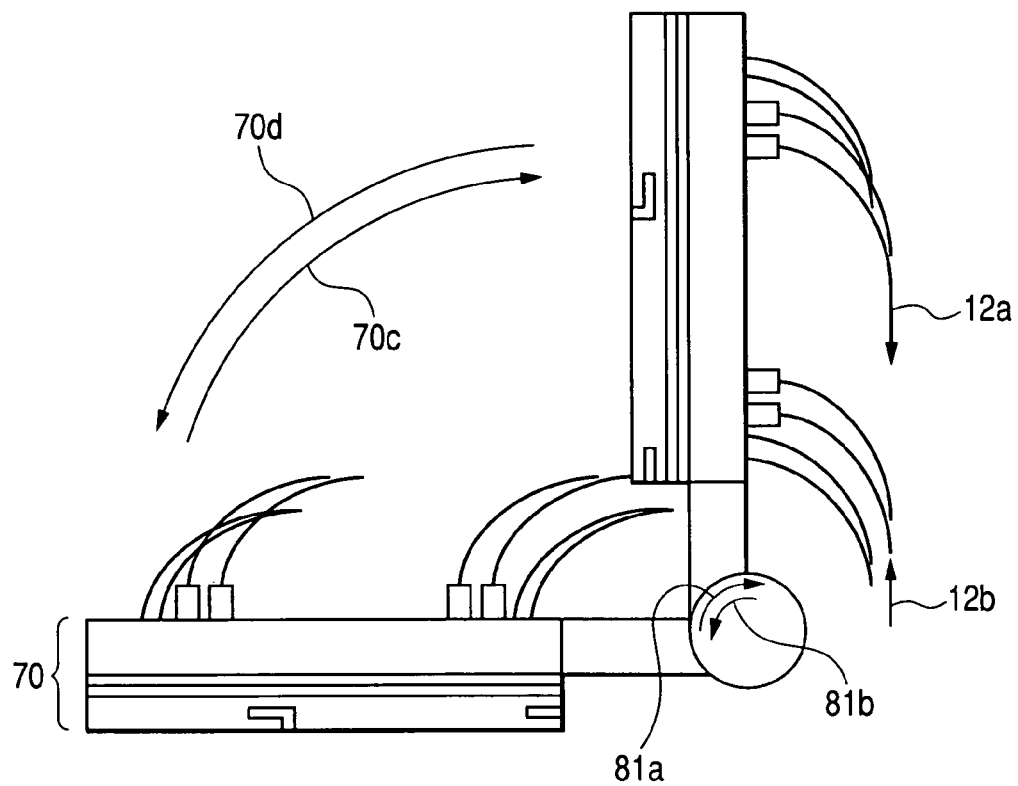

Subsequently, a method for injecting the cell suspension or medium into the culture vessel 60 will be explained with reference to FIGS. 4, 5 and 7. FIG. 4 is a front view of the seeding device 70. The joint 50 is arranged above the horizontally placed culture vessel 60. The arm 80 is attached at the side section of the joint 50, wherein the end section of the arm 80 is connected to a rotation axis 81. The rotation axis 81 can be moved in the upward direction 70a and downward direction 70b.

Upon positioning the joint 50, the tube 13 attached to the joint 50 is matched to the hole 41 formed on the culture vessel 60. As shown in FIG. 3, the tube 13 fixed to the joint 50 pushes the seal member 31b downward, so that the tube 13 is inserted into the hole 41 formed on the culture vessel 60. After the joint 50 is placed on the culture vessel 60, a suction pump not shown is driven, whereby the adsorbing pad 15 to which the suction tube 14 is connected sucks the culture vessel 60 and brings the same into intimate contact with the joint 50. This establishes an intimate contact between the second resin seal 20 and the first resin seal 30.

When the joint 50 and the culture vessel 60 are adhered with each other to compose the integral seeding device 70, the integral seeding device 70 is inclined by using the rotation axis 81. FIG. 5 is a front view of the seeding device 70. The rotation axis 81 is rotated 90 degrees in a clockwise direction 81a. The adhered culture vessel 60 and the joint 50 are rotated from the horizontal direction to the vertical direction shown by an arrow of 70c.

With this state, the medium or cell suspension is injected from the tube 12 positioned in the downward direction in the culture space 42b, i.e., from the direction shown by an arrow 12b. On the other hand, waste liquid or gas in the seeding device 70 is discharged from the tube 12 positioned in the upward direction, i.e., from the direction shown by an arrow 12a. The injected medium is the one kept in cold storage at another place. This medium is warmed up to a suitable temperature immediately before the use, and supplied to the culture space 42b with a pump not shown as afresh medium. The liquid injecting operation and liquid discharging operation are performed with the seeding device 70 standing in the vertical direction, whereby the bubbles intruded in the culture space 42b can be vented.

After a predetermined liquid is injected, the rotation axis 81 is rotated in a counterclockwise direction 81b. The integrated seeding device 70 is returned in the horizontal direction from the vertical direction. The rotation axis 81 movable in the upward and downward directions is operated, thereby setting the seeding device 70 on the base 95 shown in FIG. 1. Projections 91 that are engaged with grooves 90 are formed at the side face of the seeding device 70. Therefore, the seeding device 70 is positioned at the predetermined location before the engagement. Thereafter, the seeding device 70 is moved in the horizontal direction 92a to engage the projections 91 into the grooves 90.

The suction pump is stopped for stopping the suction from the adsorbing pad 15. Thereafter, pressure air is supplied to the adsorbing pad 15. When the pressure air is blown, resilience is caused instead of the suction force between the culture vessel 60 and the joint 50, so that the adhesion between the culture vessel 60 and the joint 50 is lost. Since the adhesion between the culture vessel 60 and the joint 50 is lost, the rotation axis 80 movable in the upward and downward directions 70a and 70b is operated in the upward direction 70a to separate the culture vessel 60 from the joint 50.

When the culture vessel 60 is lifted up in the direction of 70a, the rotation axis 80 is operated in the downward direction 70b in order that the joint 50 and the culture vessel 60 are adsorbed and adhered to each other. Thereafter, the seeding device 70 is moved in the direction 92b in which the engagement between the projections 91 and the grooves 90 is released as shown in FIG. 1. When the engagement between the projections 91 and the grooves 90 is released, the seeding device 70 is moved in the upward direction 70a, and the liquid is injected. This series of operation procedure can keep the culture space 42b in the closed state as much as possible, even if the cell suspension or medium is put into the culture vessel 60. Thus, the spill or infection from the culture space 42b can be prevented.

Figure 7:
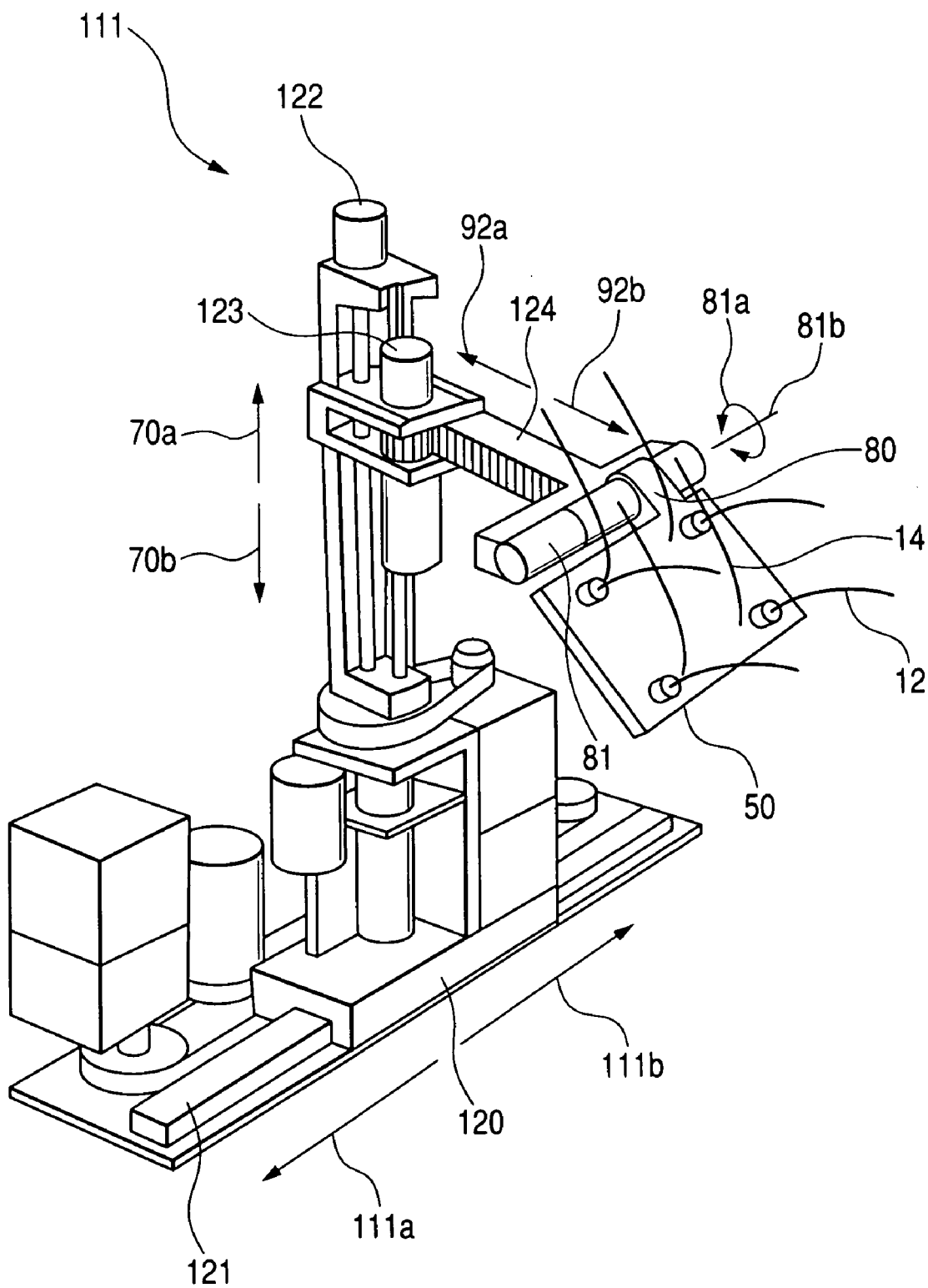
FIG. 7 is a perspective view showing a joint holder positioning section used for the culturing apparatus.

FIG. 7 is a perspective view showing a joint holder positioning section 111 used in this series of operation. A rail 121 is attached along the moving direction such that a stand 120 is movable in the forward and backward directions 111a and 111b. The stand 120 is fitted to the rail at its base section. A gear shaft 123 movable in the upward and downward directions 70a and 70b is attached to a shaft 122 of the stand 120 extending in the vertical direction. A rack 124 is meshed with the gear shaft 123, whereby the rack 124 advances or retreats in the leftward and rightward directions 92a and 92b when the gear shaft 123 is rotated. The rotation axis 81 is attached horizontally at the leading end of the rack 124 so as to be parallel to the rail. The arm 80 of the seeding device 70 can be attached to the rotation axis 80. When the rotation axis 81 is rotated, the seeding device 70 is pivoted in the directions of 81a and 81b about the rotation axis 80 extending in the frontward and backward directions 111a and 111b.

What is claimed is:

1. A culturing apparatus comprising:
   a culture vessel having a first elastic seal bonded to its upper face and having a culture space formed therein; and
   a joint provided with a supplying section for supplying solution as a medium to the culture vessel and a suction pad for pulling the culture vessel, and having bonded to its lower face a second elastic seal having a microprojection;
   wherein the first elastic seal has a valve for supplying or discharging the solution,
   wherein the second elastic seal has the microprojection, which is integrated therein and is formed at the position corresponding to the valve for preventing a spill,
   wherein the culture vessel and the joint compose a seeding device in which the first elastic seal and the second elastic seal are connected via the microprojection by the operation of the suction pad, and
   wherein each of the first elastic seal and the second elastic seal comprises an inserting section for detachably inserting a tube that is able to supply and discharge the solution.

2. The culturing apparatus according to claim 1, wherein the first elastic seal has cutouts at plural sections, wherein each cutout being used as a valve.

3. The culturing apparatus according to claim 2, wherein the second elastic seal comprises holes at the positions corresponding to the cutouts and the microprojection constituted by an annular microprojection that has a predetermined thickness and is formed around each of the holes, and
   the tube penetrates through the second elastic seal so as to be able to supply the solution to the culture space and is detachably attached to the joint.

4. The culturing apparatus according to claim 1
   wherein the suction pad is provided at the second elastic seal and is connected to a suction pump via a tube,
   wherein the culture vessel and the joint are attached to and detached from each other between the first elastic seal and the second elastic seal by the operation of the suction pump.

5. The culturing apparatus according to claim 1, wherein a water-repellant process comprises treating the surface of the valve and the microprojection.

6. The culturing apparatus according to claim 1, wherein a base on which the seeding device is placed is provided, wherein a projection is formed on the base at the position corresponding to the width of the culture vessel, a groove is provided at the side section of the culture vessel into which the projection is engaged, and the seeding device can be held by engaging the projection into the groove upon the culture.

7. The culturing apparatus according to claim 1,
   wherein an arm is provided on a side surface of the joint and a rotation axis is connected to the leading end of this arm,
   wherein, when the solution injected into or discharged from the culture space, the rotation axis is operated such that the seeding device integrally formed by the suction member is inclined from the horizontal condition.

8. The culturing apparatus according to claim 7 wherein the valve is constructed of plural valves formed at the outside of the culture space, wherein the solution is supplied from the valve positioned downward and the solution is discharged from the valve positioned upward, when the solution is exchanged.

9. The culturing apparatus according to claim 1, wherein the first elastic seal and the second elastic seal are made of viscoelastic material.

10. The culturing apparatus according to claim 1 wherein the microprojection is formed in a annular shape and is integrated with the second elastic seal.

11. The culturing apparatus according to claim 1 wherein a thickness of the first elastic seal is smaller than that of the second elastic seal.

12. A culturing apparatus comprising:
   a culture vessel having a first elastic seal bonded to its upper face and having a culture space formed therein; and
   a joint provided with a supplying section for supplying solution as a culture medium to the culture vessel and a suction member for pulling the culture vessel, and having bonded to its lower face a second elastic seal having a microprojection;
   wherein the first elastic seal has a valve for supplying or discharging the solution,
   wherein the second elastic seal has the microprojection, which is integrated therein and is formed at the position corresponding to the valve, for preventing a spill, and
   wherein the culture vessel and the joint compose a seeding device in which the first elastic seal and the second elastic seal are connected via the microprojection by the operation of the suction member,
   each of the first elastic seal and the second elastic seal comprises a plurality of inserting sections for detachably inserting sections for detachably inserting a plurality of tubes,
   an arm is provided on a side surface of the joint,
   a rotation axis is connected to the leading end of this arm,
   the rotation axis is operated such that the seeding device integrally formed by the suction member is moved from the horizontal condition to the vertical condition, when the solution is injected into or discharged from the culture space,
   gas or the solution is discharged from the valve positioned upward and the solution is supplied from the valve positioned downward in the vertical condition.

* * * * *

UNITED STATES PATENT AND TRADEMARK OFFICE
CERTIFICATE OF CORRECTION

PATENT NO.       : 7,749,750 B2
APPLICATION NO.  : 11/192023
DATED            : July 6, 2010
INVENTOR(S)      : T. Kobayashi et al.

It is certified that error appears in the above-identified patent and that said Letters Patent is hereby corrected as shown below:

Title Page, at Item (75) Inventors: delete "Kaiwagoe (JP)" and insert --Kawagoe (JP)--.

Signed and Sealed this

Twenty-eighth Day of September, 2010

David J. Kappos
*Director of the United States Patent and Trademark Office*